US011213380B2

(12) United States Patent
Noishiki

(10) Patent No.: US 11,213,380 B2
(45) Date of Patent: Jan. 4, 2022

(54) STENT GRAFT AND METHOD FOR MAKING SAME

(71) Applicant: NICEM LTD., Yokohama (JP)

(72) Inventor: Yasuharu Noishiki, Yokohama (JP)

(73) Assignee: NICEM LTD., Yokohama (JP)

( * ) Notice: Subject to any disclaimer, the term of this patent is extended or adjusted under 35 U.S.C. 154(b) by 220 days.

(21) Appl. No.: 16/588,132

(22) Filed: Sep. 30, 2019

(65) Prior Publication Data

US 2020/0038167 A1 Feb. 6, 2020

Related U.S. Application Data

(62) Division of application No. 14/770,323, filed as application No. PCT/JP2013/055767 on Feb. 26, 2013, now abandoned.

(51) Int. Cl.
*A61F 2/07* (2013.01)
*A61B 17/06* (2006.01)
*A61L 17/00* (2006.01)
*A61F 2/06* (2013.01)
*A61F 2/82* (2013.01)

(52) U.S. Cl.
CPC .......... *A61F 2/07* (2013.01); *A61B 17/06166* (2013.01); *A61L 17/00* (2013.01);
(Continued)

(58) Field of Classification Search
CPC ............... A61F 2002/075; A61L 17/00; A61B 17/06166; A61B 2017/0619; A61B 2017/0618; A61B 2017/06171
See application file for complete search history.

(56) References Cited

U.S. PATENT DOCUMENTS 7,862,583 B2  1/2011 Long
2005/0159804 A1  7/2005 Lad et al.
(Continued)

FOREIGN PATENT DOCUMENTS

JP 06007387 A 1/1994
JP 10216218 A 8/1998
(Continued)

OTHER PUBLICATIONS

English translation of Notification of Transmittal of Translation of the International Preliminary Report on Patentability and Written Opinion of the International Searching Authority (8 pages), 2015.
(Continued)

*Primary Examiner* — Brian A Dukert
(74) *Attorney, Agent, or Firm* — Flynn Thiel, P.C.

(57) ABSTRACT

A suture to be used in producing a medical instrument provided with a sutured site such as a stent graft, an artificial blood vessel or an artificial heart valve, has two components, i.e., a high melting-point component and a low-melting point component, the difference between the melting points of components being 30° C. or more and the low-melting point component is exposed on the suture surface entirely along the length direction. When a medical material formed of a fabric or a film is sutured or knotted with the suture and then the suture site is heated at such a temperature not allowing the high-melting point component but the low-melting point component alone to melt, the sutured site is fused and fixed. Thus, a knot or a seam, which sustains the fiber shape and strength and never becomes loose, can be formed.

8 Claims, 11 Drawing Sheets

(52) U.S. Cl.
CPC ... *A61F 2002/065* (2013.01); *A61F 2002/075* (2013.01); *A61F 2002/826* (2013.01); *Y10T 156/10* (2015.01)

(56) References Cited

U.S. PATENT DOCUMENTS

| | | |
|---|---|---|
| 2007/0255422 A1 | 11/2007 | Wei et al. |
| 2009/0216269 A1 | 8/2009 | Harrington et al. |
| 2013/0226234 A1* | 8/2013 | Avelar .................... D04C 1/12 606/231 |

FOREIGN PATENT DOCUMENTS

| | | |
|---|---|---|
| JP | 2000080550 A | 3/2000 |
| JP | 2005187954 A | 7/2005 |
| JP | 2008110195 A | 5/2008 |
| JP | 2009535101 A | 10/2009 |
| JP | 2009536044 A | 10/2009 |
| JP | 2009269821 A | 11/2009 |
| JP | 2010070868 A | 4/2010 |
| JP | 2011136091 A | 7/2011 |
| WO | 2006088163 A | 8/2006 |

OTHER PUBLICATIONS

English translation of International Search Report issued in Application No. PCT/JP2013/055767 dated Apr. 2, 2013 (2 pages).
Kuraray Vectran Properties: Thermal Properties Brochure, 2017.
Polymer Properties Database: Melting Points of Polymers; polymerpropertiesdatabase.com, 2015.

* cited by examiner

STENT GRAFT AND METHOD FOR MAKING SAME

CROSS-REFERENCE TO RELATED APPLICATIONS

This is a divisional of prior U.S. application Ser. No. 14/770,323, filed Aug. 25, 2015, which is a National Phase application of PCT Application No. PCT/JP2013/055767, filed Feb. 26, 2013, the entire contents of which is hereby incorporated herein in its entirety.

FIELD OF THE INVENTION

The present invention refers to sutures used in creating medical devices having sutured parts, in particular, medical devices for in vivo implantation. The present invention presents a method for using such sutures and medical devices sewn together by these sutures.

DESCRIPTION OF PRIOR ARTS

Many highly mobile medical devices are sutured by hand during their creation. For example, when creating an artificial vascular graft with a branch, a small-diameter artificial vascular graft is sutured onto a large-diameter artificial vascular graft. In the case of an artificial valve, fabric made of polyester fibers is sewn to a metal wire ring so as to be easily sutured to the heart wall. In a case of a stent graft, an expanding part made of metal wire mesh is fixed to a tube fabric by suturing. Thus, some kind of suturing is generally used when creating highly mobile medical devices. This suturing is performed by either a continuous or interrupted suturing method which involves forming knots with each needle stitch.

When surgeons tie sutures during a surgical operation, they try to make knots that will not become loose. In vivo, cells invade the gaps among fibers of the ligatured part, which prevents the knots from becoming loose. In the case of artificial medical devices, however, there is certain time lag from the day of preparation to the day of actual use, and sutured seams or knots in the sutures may become loose during the delay. Especially in the case of medical devices used in the cardiovascular field, for example, heart valves, artificial vascular grafts and stent grafts, are highly mobile and have a complicated shape. Consequently, there are more sites to be sutured. Since the time from preparation to actual use is long, sutured seams or knots in the sutures may become loose. If a medical device with such loose seams or knots is implanted in vivo, there are strong tensile stress loads to the medical device with each pulsation. This repeated stress after implantation may accelerate the loosening of the seams or knots. If the seams or knots become loosened, the device cannot function properly, with very serious consequences. Therefore, during the preparation process, it is necessary that each suture should be tied tightly and repeatedly. Nevertheless, up to the present time, the problem of loose seams or knots has not been satisfactorily solved.

A stent graft is presented as a specific example. In the case of a stent graft, after an expanding part made of wire mesh is sewn to a fabric made of synthetic fibers, the stent graft is folded into a thin shape, inserted into a fine sheath and pushed forward along the narrow sheath wall. There is a danger that the ligature knots will become loosened by rubbing against the sheath wall during insertion, consequently shifting the position of the expanding part of the mesh. To avoid the occurrence of such an accident, each suture needs to be tied tightly and repeatedly, several times or more. This makes the knots more bulky, and causes them to catch inside the sheath. When a stent graft is inserted into a sheath, sutured parts with bulky knots receive extra tensile stress by rubbing against the sheath wall, which may hasten the loosening of the knots. Thus separation of the expanding part of the wire mesh from the fabric might easily occur. This kind of accident might occur unexpectedly in a patient who has received a stent graft implantation. To obviate this danger, knots are made as tightly as possible, but at the same time, from the point of view of folding a stent graft as thin as possible, bulky and repeatedly tied knots are undesirable, as stated above. This fearful dilemma remains unsolved.

Techniques for avoiding the loosening of sutured sites have already been proposed. For example, in patent document 1, a knee joint supporter made of a flexible pad and a cylindrical fabric band is proposed. The pad is fixed with heat fusible sutures in order to fix the flexible pad to the fabric band. By using heat fusible fibers (e.g., nylon), the fibers adhere to one another and become difficult to separate. Thus, it is reported that a durable supporter for sports use can be fabricated. In this technique, a thread made of thermofusible fibers having a low-melting point is heated and the fibers are made to adhere to one another without destroying the original structure of the fabric. The fibers of the suture are fused by heat and the melted fibers lose their shape. Thus the sutures described in patent document 1 cannot maintain their shape or strength. In patent document 2, a bone implantation device using heat fusible sutures is described. It is stated that this device can be created after the heat fusible sutures are melted, and a suitable shape for the device can be formed.

In reported techniques, the fibers of the sutures are fused and are practically glued together. Therefore, the sutured part is heat-fused and the shape of the fibers disappears. It is already known that medical devices for in vivo implantation are subjected to tensile stress on their sutures. In the cardiovascular system, tensile stress is brought to bear by each pulsation, and strongly affects the sutures. Sutures in the cardiovascular system are required to maintain sufficient strength as long as the patient lives. In medical devices implanted in vivo, the sutures need to have good durability and maintain their strength, to prevent seams or knots from loosening. Especially in the cardiovascular system, sutures of implanted medical devices are made of a material that will not deteriorate.

In patent document 3, an artificial vascular graft with heat fusible sutures is described. That is, in a cylindrical fabric tube made of synthetic fibers, heat fusible sutures are partially braided, woven, incorporated, or interlaced into the tube material. Then the cylindrical fabric is heated so as to fuse the heat fusible fibers, making them adhere to each other and protect the cut edges of the fabric from fraying. As a heat fusible fiber, polyester copolymer fiber having a lower melting point than regular polyester fibers which are used for artificial vascular grafts is mentioned as examples. So called polyester/polyolefin sheath-core hybrid type fibers and polyolefin fiber or polyester/polyolefin side-by-side hybrid type fibers are mentioned. These fibers are heat fusible fibers in the fabric, which are then heated to fuse them and protect the fabric from fraying.

In another application of heat fusing fibers, patent document 4 describes a technique to obtain a woven cloth belt which resists deformation. Sheath-core hybrid type fibers composed of a no heat fusing component and a heat fusing component are fused by heat to amalgamate the fusible fibers. Further, in patent document 5, a technique to mix sheath-core hybrid type fibers composed of a high-melting point component and a low-melting point component in an unwoven fabric is proposed. In these previously reported techniques, ideas to prevent fraying of the fabric cut edge are reported. However, these documents do not address the problem of maintaining sufficient suture strength and shape.

PREVIOUSLY REPORTED TECHNIQUES

Patent Document 1: JP2010-70868A Publication
Patent Document 2: JP2011-136091A Publication
Patent Document 3: JPH6-7387 A Publication
Patent Document 4: WO2006/088163 Publication
Patent Document 5: JP2000-80550A Publication

BRIEF SUMMARY OF THE INVENTION

Object of the Invention

The present invention is performed concerning the above-mentioned circumstances. The present invention relates to a suture used for the manufacture of a medical device having a sutured site (hereinafter, mentioned as 'suture for medical device'). The object of the present invention is to provide a suture by which a sewing process can be performed safely and surely, and to obtain a seam or knot which does not become bulky and does not loosen, maintaining the original shape and strength of the suture. The present invention also provides how to apply the suture, and further, medical devices sewn by this method.

Brief Illustration of the Invention

The present inventor repeated earnest studies and experiments, and achieved the object stated above by using the suture. The suture contains high-melting point component fibers with a low-melting point component. The difference of the melting points of them is 30° C. or more.

That is, the present invention is a suture for sewing a medical device comprising, a high-melting point component and a low-melting point component, wherein the difference of melting points between said high-melting point component and low-melting point component is 30° C. or more and the low-melting point component is exposed on the suture surface along its whole length. The suture is desirably a hybrid multifilament which contains high-melting point component fibers with a low-melting point component. The hybrid multifilament is desirably selected from a group consisting of side by side type, sea-island type, dividing type and sheath-core type. Desirably, the high-melting point component fibers are coated with a low-melting point component, or the fibers have a low-melting point component in their interstices. Still further, the suture desirably has a thermal shrinkage feature. Yet further, the suture desirably has a needle installed. One end of the suture is inserted into a hole of a needle tail and swaged.

The present invention is a method for the heat-fixing of a sutured site of a medical device made of fabric or film at a temperature that melts a low-melting point component but does not melt a high-melting point component. The present invention is a method for the heat-fixing of different kinds of medical fabrics, films, or metals by suturing with the suture. After suturing, all seams and knots of the suture are fused by heat and fixed, since only a low-melting point component of the suture melts and high-melting point component fibers maintain its original shape and strength.

The present invention also relates to a stent graft prepared by suturing synthetic fiber fabric with a NiTi-based alloy wire using the suture. Further, the present invention is a stent graft prepared by suturing a polyester fabric which has a low-melting point component in the interstices of fabric fibers before the suturing is performed. A NiTi-based alloy wire is sutured, using the suture and fixed by heat fusion on the sutured site at the temperature that melts a low-melting point component but does not melt a high-melting point component.

The present invention relates to an artificial fabric vascular graft made of polyester fiber prepared by suturing a bifurcated trunk and/or a branch to the graft with the suture. Then the graft was heated for the heat-fixing of the sutured sites. The present invention is an advanced method to connect a bifurcated trunk and/or a branch on a fabric vascular graft made of polyester fiber. The suture is incorporated in both anastomotic sites of the fabric graft and a cut end of the branch. Then anastomosis is performed with the suture. Knots and seams at the anastomotic sites of the suture are heat-fixed.

Effect of the Invention

The suture for sewing a medical device of the present invention contains two components, that is, a high-melting point component and a low-melting point component, wherein the difference of the melting points between the two components is 30° C. or more. The low-melting point component is exposed on surface of the suture along its entire length. After being sown by the suture, the low-melting point component can be melted without melting the high-melting point component by heat treatment. Thus, seams or knots can be fixed, and do not become loose. Even after fusing, since the high-melting point component maintains the original fabric shape and strength, seams or knots can maintain their strength. Further, if the suture of this invention has a thermal shrinkage feature, knots become more tight and adhesion by heat fusion becomes more firm.

During a manufacturing process, a safe medical device can be made by suturing with the suture of the present invention by either continuous or interrupted suturing. At an adequate heat treatment, a low-melting point component melts, but a high-melting point component fibers do not melt. After all seams or knots are fixed by heat, they do not become loose. In a case of an artificial heart valve, the method can prevent a suture ring from peeling off the fabric mesh of its suture ring. In a case of an artificial vascular graft, sewing of a branch can be performed more safely. In a case of a stent graft, without excess rubbing against the inner wall of the sheath, less bulky knots makes inserting into a fine sheath easy, and a finer sheath can be selected. In a case of a stent graft, certain sewing with the suture can prevent all the knots and seams from loosening, even under continuous tensile stress of pulsation. Besides, the suture with a needle is good at handling.

PREFERRED EMBODIMENT OF THE INVENTION

Figure 1:
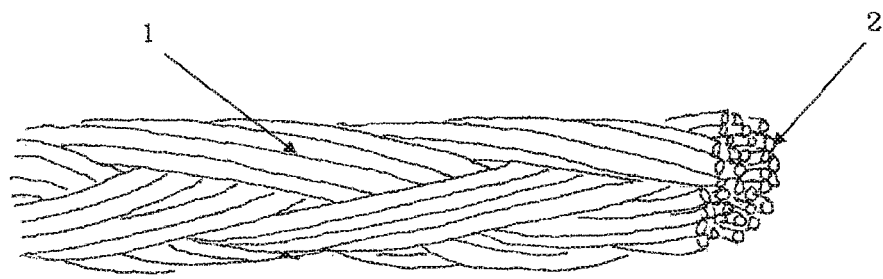
FIG. 1 shows an example of a conventional multi-filament suture.

The present invention is a suture for sewing medical devices. The suture has two components, namely, a high-melting point component and a low-melting point component. The difference between the two melting points is 30° C. or more, and the low-melting point component is exposed on the thread surface along its entire length. After suturing with this suture, the low-melting point component on the surface of the suture is melted, and the seam or knot is fused, and fixed, thus preventing the seam or knot from becoming loose. At the same time, the high-melting point fiber does not fuse and serves to maintain the state of the fiber; that is, the shape of a seam or knot remains tight, and their mechanical strength can be maintained.

When this suture is used for sewing a medical device, heat treatment makes the low-melting point component melt and fuse, fixing not only the sutures but also the adjacent threads of fiber at a seam or a knot. Therefore, it is desirable to expose the low-melting point component along the entire length of the suture. That is, the low-melting point component should be coated over the surface of the suture along its entire length. The larger the exposed area of the low-melting point component is, the more easily it is fused. In cross section, the low-melting point component can cover the surface of the section wholly or in part. The exposed part of the low-melting point component may be 5-100% of the surface area; the ideal is 10-100%.

As high-melting point and low-melting point components, any material such as that used for ordinary surgical purposes can be used, that is, any material which has a good stability in vivo and is biocompatible. Ideally, polyester, polyamide, polyolefin, polyurethane, or polytetrafluoroethylene should be used. These are high molecular compounds. Compounds whose melting points differ by 30° C. or more can be combined directly, or after modification of the components of copolymerization.

Here, methods for preparation of the suture of the present invention are explained. The first method is as follows. Filaments with a high-melting point, and filaments with a low-melting point which is lower than the high-melting point filaments by 30° C. or more are prepared. These two kinds of filaments are combined to make a suture ideally by twisting, braiding, or warp knitting. In other words, a suture can be created by ordinary twisting, warp knitting, knitting, three axis knitting, or braid over braid. Any method can be used for combining filaments, but it is necessary to expose the lower melting point component to the surface of the suture along its entire length in order to obtain the fusing effect. In any case, it is necessary that the high-temperature-melting component does not fuse, so that it can maintain the shape and strength of the suture.

The second method is as follows. Filaments with a high-melting point are prepared, and they are coated with a material having a melting that is 30° C. or more lower. As the high-melting point component, monofilament or multi-filament fibers can be used, as long as they are strong enough and easy to handle. When a multifilament fiber is used, the low-melting point component penetrates the fibers of the high-melting point component during the coating process.

The low-melting point component not only coats the surface but also fills the spaces between filaments. If the penetration is deep enough, the multifilament component functions as a single filament, possessing a moderate toughness which is good for sewing. If the penetration is too shallow, the suture becomes too soft to handle. The degree of penetration can be regulated by changing the thickness of the suture. In any case, coating with a low-melting-point component is effective for fixing by fusion. In any case, the high-melting point component does not fuse, and the shape and strength of the suture is maintained. For coating with a low-melting point component, the suture can be immersed into a solvent containing the low-melting point component in solution. The coating can also be done with a knife coater or a gravure coater while the low-melting point component is melted by heat. When deeper penetration is needed, liquid coating or penetration is preferable. However, some solvents destroy the characteristics of the high-melting point component. In this case, the heating method is preferable.

The third method is a technique creating a conjugate multifilament fiber with two components, namely, a high-melting point component and a low melting point component. The method produces filaments which have a suitable thickness and strength as sewing sutures. Cross-sections of the conjugate filament, can be of the side by side type, sea-island type, separation type, or sheath-core type. The fiber disclosed in patent document 4 can also be used, and it can be also used as a thick monofilament. When an incorporated filament is used, the surface area of the suture should be covered with part of a low-melting point component to fix it effectively by fusion. For example, in the case of a sheath-core type or a sea-island type, a high-melting point component is used as a sheath or the island part and a low-melting point component is used as a matrix or sea part. In the case of a side by side type or a separation type, both components appear mutually on the surface of the filament, resulting in a smaller exposed ratio of the low-melting-point component on the suture surface, and sometimes in insufficient fixing by fusion. In such cases, it is necessary to consider increasing the ratio of the low-melting point component. One of the advantages of using a conjugated filament is the possibility of even using an in-vivo toxic and/or in-vivo deteriorative high-melting point component as a reinforcing material. That is, the use of such an in-vivo toxic and/or in-vivo deteriorative high-melting-point component as the core part of the sheath-core type or the island part of the sea-island type, and the use of a low-melting point component without in-vivo toxicity or in-vivo deterioration as the sheath part or the matrix prevents direct contact with a living body by an in-vivo toxic and/or in-vivo deteriorative high-melting-temperature component.

In the present invention, the terms "high-melting point or low-melting point" components are relative, and signify solely that the melting points of two components differ by 30° C. or more. However, in actual fact, the ideal melting point of a high-melting point component is 220° C. or more, and 250° C. or more is even more desirable. On the other hand, the ideal melting point of a low-melting point component is 120° C.-220° C., or even 170° C.-210° C., but these temperatures are not absolute. Specifically, as high-melting point components, polyester, polyamide, polyolefin, polyurethane, or polytetrafuluoroethylene are suitable, and they are usually used as medical material. However, the choice is not limited to these components, and any kind of material with a good stability in vivo and good biocompatibility can be used in the present invention. As a low-melting point component, components which are of public knowledge and meet the conditions stated above can be used. In particular, any polyester copolymer which uses adipic acid, sebacic acid or isophthalic acid, with polyetherglycol or butyleneglycol as a copolymerization component, or polyolefin and any of its polymers can be used.

As the suture of the present invention, a monofilament or a multifilament fiber of 30-3000 dtex fineness is desirable, and the number of filaments can range from 1 to 500. Actually, sutures that have a thickness of 6-0 to 4 (JIS-T4101 unit), as indicated by the Japan Pharmaceutical Affairs Law, are sufficiently usable. The fineness of a suture is desirably within the range of 53-5300 dtex, and the tensile stress is desirably within the range of 2-50 Newton. In the present invention, a monofilament or a multifilament fiber with good usability can be used. The usability of a suture regarding its stiffness can be numerically expressed by the cantilever method. The stiffness of the suture of the present invention, although it depends on the thickness of the suture, is ideally 3-15 cm by the cantilever method, and 4-10 cm is even better.

In the present invention, a medical device sutured with a suture of the present invention, for example, an artificial vascular graft, heart valve, or stent graft, is heated at a temperature that does not affect the characteristics of the high-melting point component but can melt the low-melting point component. The conditions of heating, that is, a suitable temperature and duration can be selected by trial and error. The range of the selection is between where the low-melting point component is completely melted and where the low-melting point component adheres partially to itself and the surroundings. For heat treatment, an ordinary hot-air dryer, a heat blaster, or a hot-air sterilizer can be used. A further desirable trait of the present invention is thermal shrinkage. Thermal shrinkage after knots are tied tightens the knots further, and fixation by fusion becomes stronger. The ideal thermal shrinkage ratio is 5% or more, and 10% or more is even better. To attain this thermal shrinkage ratio, it is effective to use filaments drawn at a lower temperature or to use filaments composed of copolymerized polymer.

In conventional techniques for making a suture to be used in the preparation of a medical device, little attention has been paid to prevention of the loosening of a seam or a knot. In the present invention, the improvement of a suture for medical devices is proposed, especially for use in a cardiovascular device to which a tensile stress is applied repeatedly and continuously. The present invention introduces a heat fusion technique for creating a suture which can prevent a seam or a knot from loosening, and which does not cause loss of the suture's original strength and shape, even when subjected to such a tensile stress in the cardiovascular system. Medical materials made of fabric in the present invention are, for example, knitted, woven or non-woven fabrics made of polyethylene terephthalate fibers. Medical materials in the present invention having a film are, for example, polyethylene terephthalate films or sheets.

The present invention will be illustrated more in detail by drawings.

Figure 2:
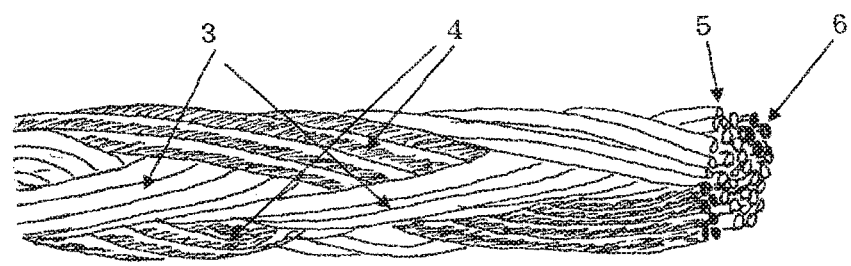
FIG. 2 shows an example of a suture for sewing a medical device according to the present invention in which a multi-filament fiber is used.

FIG. 1 shows an example of a conventional suture. 1 is a bundle of fibers composed of multifilament, and 2 is a cross-sectional view of the suture. Ordinary sutures other than sutures of monofilament fiber made of nylon or polypropylene have the braid structure shown in the drawing. On the other hand, FIG. 2 shows an example of a suture for sewing a medical device according to the present invention in which a multifilament is used. In the drawing, 3 shows a strong multifilament fiber composed of a high-melting temperature component, 5 shows the cross-sectional view thereof, 4 shows a multifilament fiber composed of a low-melting point component, and 6 shows the cross-sectional view thereof. A multifilament fiber composed of a high-melting point component 3 and a multifilament fiber composed of a low-melting point component 4 are braided in together to form one suture. By using two bundles of a multifilament fiber composed of a low-melting point component 4, the multifilament fiber composed of a low-melting point component 4 is exposed on the surface of a thread along its entire length, since these two bundles 4 are mutually exposed on the thread surface. As clearly understood by the cross-sectional view of the thread, a low-melting point component 4 is arranged so as to occupy part of the surface of the cross-section of the thread.

Figure 3:
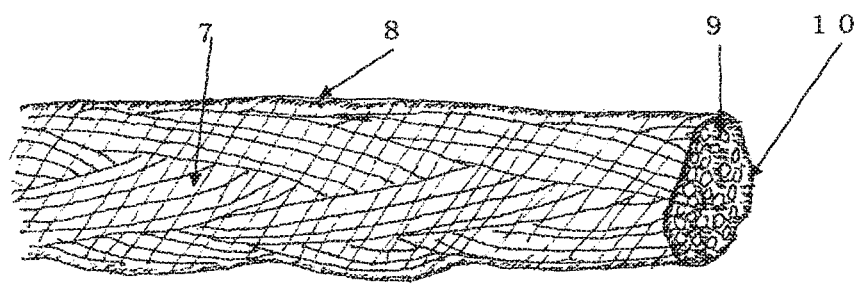
FIG. 3 shows an example of a suture for sewing a medical device according to the present invention in which fibers were coated and impregnated with a low-melting point polymer on high-melting point component filaments.

FIG. 3 shows another example of a suture for sewing a medical device according to the present invention composed of a multifilament fiber. In the drawing, 7 shows a strong multifilament fiber composed of a high-melting point component, 9 shows a cross-section thereof, 8 shows a low-melting point component covering the whole suture surface, and 10 shows a cross-section thereof. A low-melting point component 8 not only covers the whole surface of a multifilament composed of a high-melting point component 7, but also penetrates into gaps among filaments. A low-melting point component 8 is exposed on the surface of the thread along its entire length. The cross-sectional view of the thread also shows a low-melting point component 8 is arranged so as to be exposed on the whole cross-sectional surface of the thread.

Figure 4:
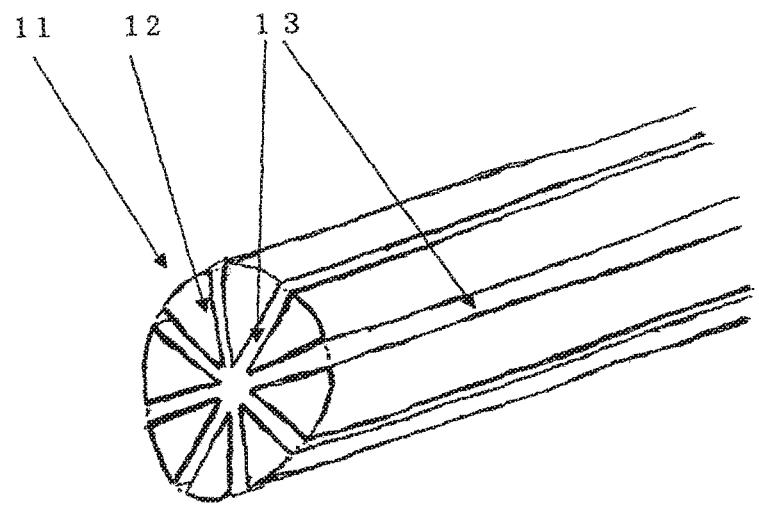
FIGS. 4-7 shows hybrid type filaments used as sutures for sewing a medical device according to the present invention.
Figure 5:
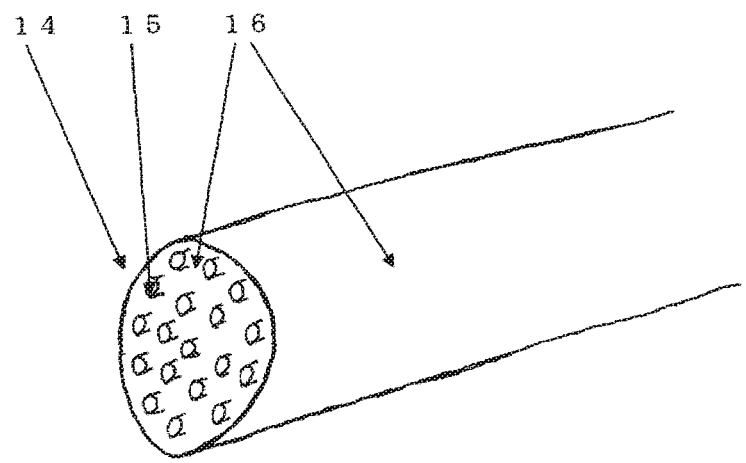

FIG. 4 shows one example of a divided-type hybrid filament which contains a high-melting point component and a low-melting point component. In the drawing, 11 is a cross-sectional view of a filament, which is similar to that of an orange, 12 is a high-melting point component, and 13 is a low-melting point component. By heat treatment, a high-melting point component 12, which has a triangle cross-section, maintains the strength and shape of the suture, while a low-melting point component 13 melts and fuses the surrounding fibers. FIG. 5 shows one example of sea-island type hybrid filament composed of a high-melting point component and a low-melting point component. In the drawing, 14 is a cross-sectional view of the filament thereof, which has a look of many islands in a sea. The island parts 15 are a high-melting point component, and the sea part 16 is a low-melting point component. By the heat treatment, fibers of a high-melting point component remain unchanged, and a low-melting point component melts and fuses the surrounding fibers.

Figure 6:
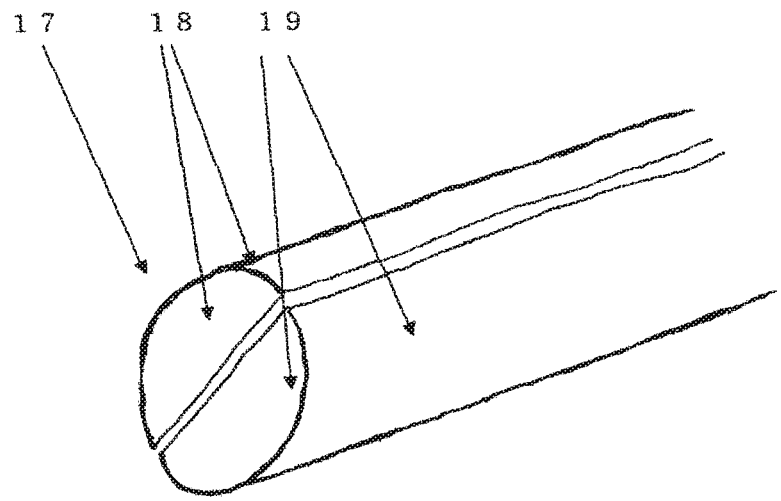
Figure 7:
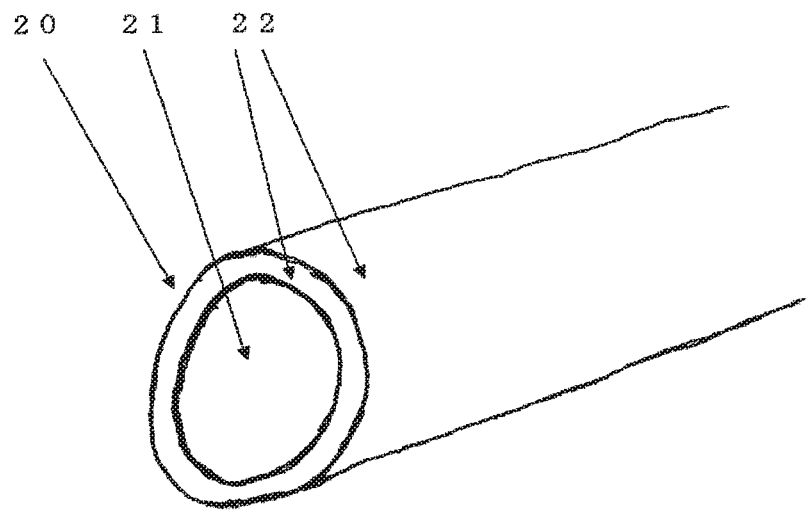

FIG. 6 shows one example of a side-by-side type hybrid filament composed of a high-melting point component and a low-melting point component. In the drawing, 17 shows a cross-sectional view thereof, which has two semicircles that appears to be put back to back, and 18 is a high-melting point component, while 19 is a low-melting point component. By heat treatment, a semicircle fiber 18 of a high-melting point component remains unchanged, and the other semicircle 19 of a low-melting point component fuses and adheres to the surrounding fibers. FIG. 7 shows one example of sheath-core type hybrid filament composed of a high-melting point component and a low-melting point component, and 20 is a cross sectional view thereof, which appears as if a core axis is surrounded with a sheath. In the drawing, 21 is a high-melting point component, and 22 is a low-melting point component. By heat treatment, an axis part of a high-melting point component 21 remains unchanged, while a sheath part of a low-melting point component 22 fuses and adheres to the surrounding fibers.

As shown in FIGS. 2-7, the suture according to the present invention is composed of a high-melting point component and a low-melting point component. As shown in FIGS. 4-7, a hybrid filament can be used in form of a mono filament and multifilament fiber, as a suture. Further, as shown in FIG. 2, a multifilament fiber composed of a high-melting point component and a low-melting point component can be formed to one suture by a braiding or twisting technique. Furthermore, as shown in FIG. 3, by coating and/or infiltration of a low-melting point component onto a high-melting point component, it is possible to form one suture having two components. In any case, a high-melting point component is strong enough to maintain the strength as a suture, and it is necessary that a low-melting point component occupy at least part of the surface of said suture, for the purpose for improving the fusing effect involving the surrounding fibers.

Figure 8:
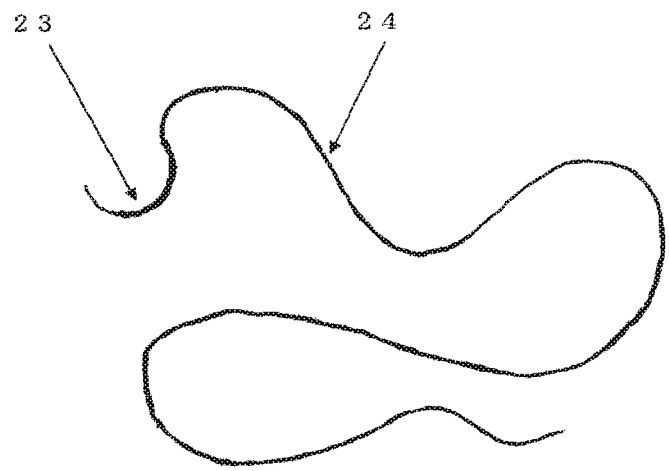
FIG. 8 shows an example of a suture with a needle for sewing medical devices according to the present invention.

FIG. 8 shows a suture for sewing a medical device to which a sewing needle is installed. In the drawing, 23 is a metal needle, and 24 is a suture for sewing a medical device. A single use of the suture for sewing a medical device according to the present invention is feasible. In the present invention, however, the suture accompanied with a sewing needle is recommended, since the presence of a sewing needle will improve usability while suturing. The style of suture with a sewing needle can make a suturing operation smooth, and the size of a hole after the suture passing through to a minimum. To install the needle, a needle 23 having a tube tail part is used, and one end of the suture is inserted into the tube tail part and fixed it by swaging.

Figure 9:
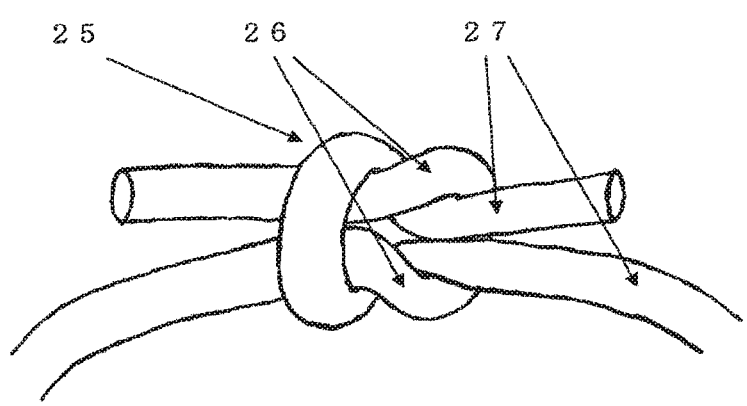
FIG. 9 shows the state of a knot of an ordinary suture.
Figure 10:
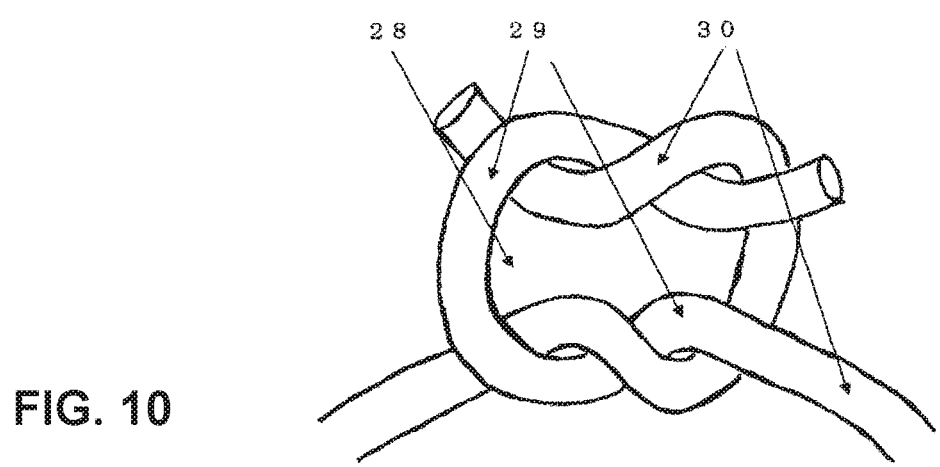
FIG. 10 shows a loosened knot of an ordinary suture.

FIG. 9 is an image showing a knot formed by a suture. Suture 26 and suture 27 are tied, and form a knot 25. FIG. 10 shows that the knot shown in FIG. 9 has become loose, and 28 is the loosened knot. When a knot formed by a suture 29 and suture 30 become loose, the seam or knot which was tightly sewed together will become loose.

Figure 11:
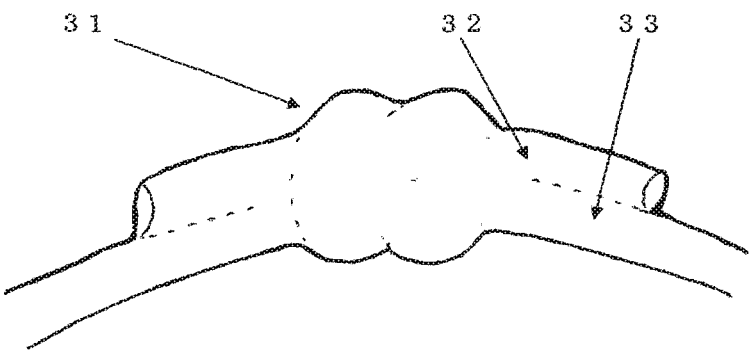
FIG. 11 shows the fused and fixed state of the knot of a suture according to the present invention.

FIG. 11 shows the melted and fused state of a knot by heat treatment at the elevated temperature to the temperature which does not melt a high-melting point component, but can melt a low-melting point component, after forming the knot shown in FIG. 9 using the suture for sewing a medical device according to the present invention. As shown in FIG. 11, a knot 31 formed by a suture 32 and suture 33 becomes unified by fusion of a low-melting point component, and the cut ends of the threads will approach the nearby thread by surface tension. When the temperature falls, the knot is strongly adhered by heat fusion, never to loosen. As shown on FIG. 9, after tying a suture and making a knot, there is a fear that the knot will loosen as shown on FIG. 10. According to the present invention, however, only a low-melting point component composing the suture fuses, while a high-melting point component maintains the shape and strength of the thread. Thus, the mobility of the suture can be maintained and protect a knot from loosening.

Figure 12:
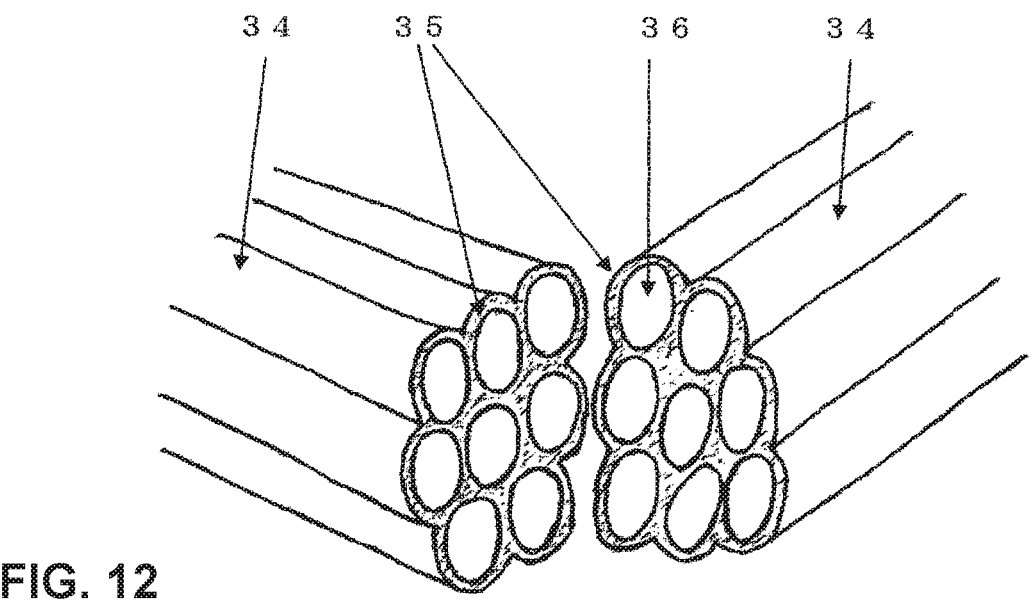
FIG. 12 is a cross-sectional view of the contact point of two high-melting point fibers coated and impregnated with a low-melting point polymer.

FIG. 12 shows a cross-sectional view of the contact point of a sutures for sewing a medical device according to the present invention. In the drawing, 34 is a suture characterized in that multifilament fibers of a high-melting point component are coated with a low-melting point component, and 35 is a low-melting point component resin, while 36 is a high-melting point component filament. The cross-section shows the state that each multifilament of a high-melting point component is coated with a low-melting point component. All gaps among filaments do not need to be occupied by the resin, but the effect of the present invention can be fully displayed by coating with a low-melting point resin.

Figure 13:
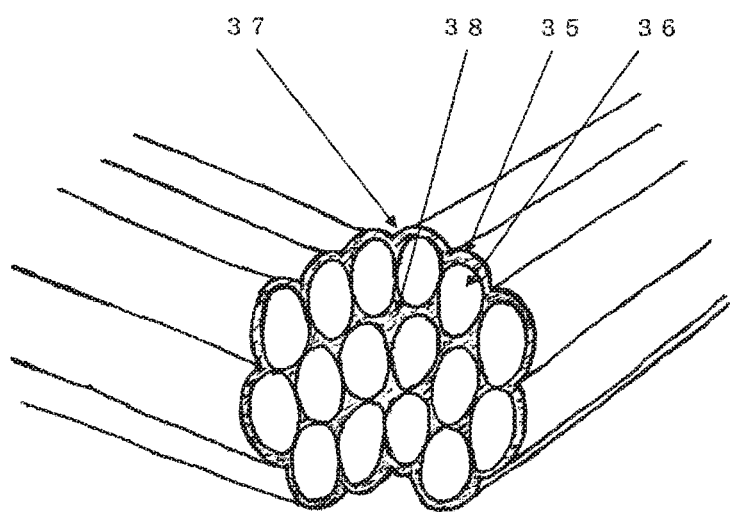
FIG. 13 is a cross-sectional view of the fused state of the two multi-filament fibers shown in FIG. 12 at the point where they intersect.

FIG. 13 shows a schematic drawing of the state of a multifilament fiber coated by the low-melting point resin of FIG. 12 after being heated at a temperature which can melt only a low-melting point component, but a high-melting point component does not melt. In the drawing, 37 is a cross-section showing the fused state, 35 is a low-melting point component, while 36 is a high-melting point component, and 38 shows the state that the melted low-melting point component is solidified by cooling, and the two multifilament fibers are fused. Even in this state, the strength as a suture is not deteriorated, since a high-melting point component 35 exists inside with a low-melting point component being adhered.

Figure 14:
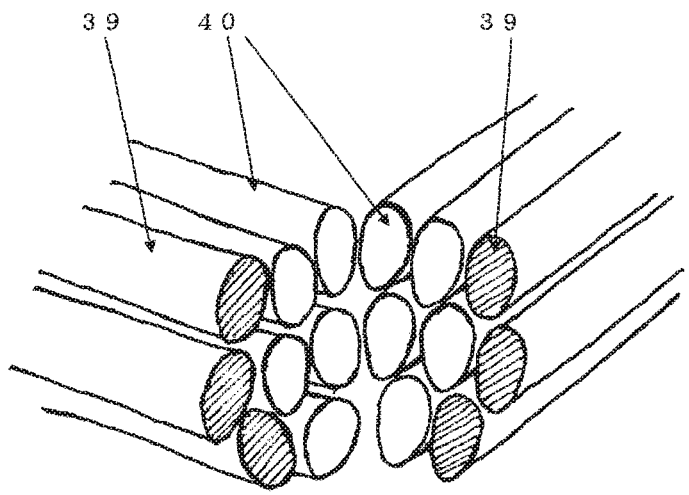
FIG. 14 is a cross-sectional view of the contact point of multi-filament fibers composed of high-melting point and low-melting point fibers.
Figure 15:
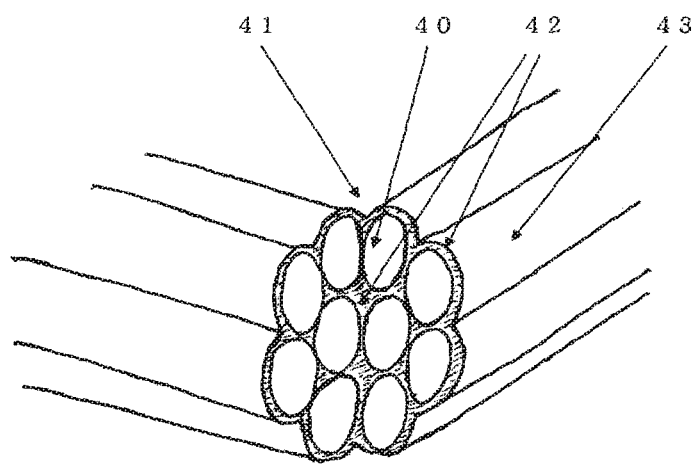
FIG. 15 is a cross-sectional view of the fused state of the multi-filament fibers of FIG. 14 at their contact point.

FIG. 14 shows a cross-sectional view of the contact point of the suture for sewing a medical device. In the drawing, 39 is a filament of a low-melting point component, and 40 is the filament of a high-melting point component in FIG. 2. Shown in the sectional view, these filaments are mixing together. FIG. 15 shows a cross-sectional view of the contact point shown in FIG. 14, after heat treating at the temperature that makes a low-melting point component melt, but a high-melting point component not melt. In the drawing, 40 is a high-melting point component, 41 is a cross-section of the fused state, and 42 shows the state that the low-melting point component is solidified by cooling, and the two multifilament fibers are fixed. Even in this state, the strength as the suture is not deteriorated, since a high-melting point component 40 exists inside with a low-melting point component being fixed.

Figure 16:
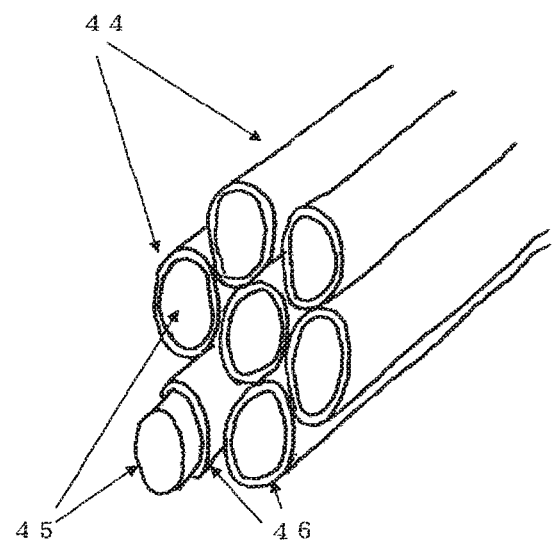
FIG. 16 shows an example of a suture for sewing a medical device composed of sheath-core type hybrid filaments made according to the present invention.

FIG. 16 shows a section of an example of a suture for sewing a medical device composed of a hybrid filament of a high-melting point component and a low melting point component. Among various types of hybrid filaments such as side-by-side type, sea-island type, dividing type or sheath-core type, the sheath-core type hybrid filament is selected as their representative, and a suture for sewing a medical device composed of said hybrid filament shown in FIG. 7 is illustrated as an example. FIG. 16 shows a suture of multifilament fibers, however, a thicker mono filament can also display the effect of the present invention. In the drawing, 44 is a multifilament, and each of them has a core axis and its cylindrical covering. The core axis 45 is composed of a high-melting point component, and the covering part 46 is composed of a low-melting point component.

Figure 17:
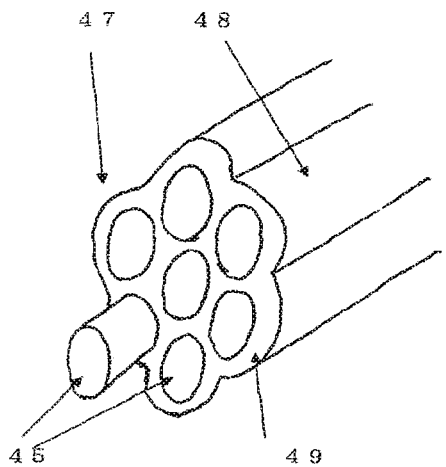
FIG. 17 shows the state after heat treatment of FIG. 16. The low-melting point polymer has melted, but the high-melting point fibers have not.

FIG. 17 shows the state of the suture for sewing a medical device composed of sheath-core type hybrid multi filament shown in FIG. 16 after heating at the temperature that a low-melting point component melts but a high-melting point component does not melt. In the drawing, 47 is the cross-sectional view thereof, and 49 is the state of a low-melting point component being melted by heat treatment, and solidified by cooling. Although the multifilament appears as if it is a mono filament, since a high-melting point component 45 remains unchanged inside with a low-melting point component being fixed.

Figure 18:
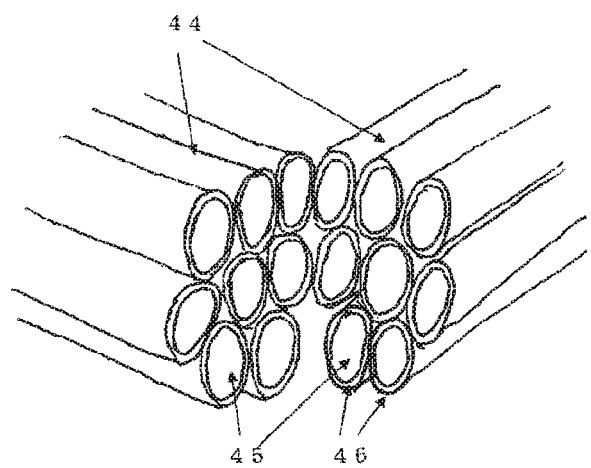
FIG. 18 is a cross-sectional view of the contact point of the two multi-filament fibers shown in FIG. 16.
Figure 19:
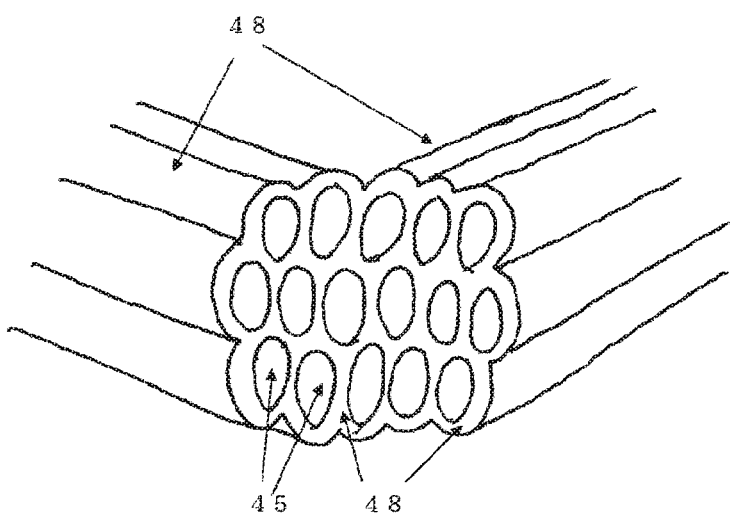
FIG. 19 is a cross-sectional view of the fused state of the multi-filament fibers of FIG. 18 at their contact point.

FIG. 18 is a cross-sectional view of the contact point of the two sutures for sewing a medical device composed of sheath-core type hybrid filament shown in FIG. 16. Each thread has a core axis 45 of a high-melting point component, and a sheath 46 of a low-melting point component. FIG. 19 shows a cross-sectional view of the contact point of the two sutures of FIG. 18, where a low-melting point component has melted, but a high-melting point component does not melt. Said hybrid filament, in which a core axis part of a high-melting point component is coated with the sheath part of a low-melting point component, is unified after heat treatment, with a high-melting point component 45 remaining inside, surrounded by the fused low-melting point component 48, which appears to be a mono filament. In this way, only heat treatment on a cross point of two sutures can firmly fuse to one body without tying them together. Of cause, if the sutures are tied together to make a knot, the hybrid filaments of a knot is fused and fixed firmly. Thus, a stronger tie can be obtained.

Figure 20:
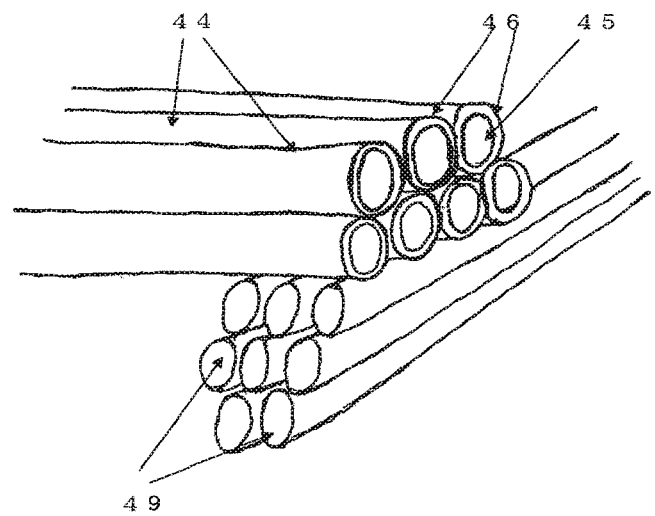
FIG. 20 shows the intersectional point of the sutures of FIG. 16 and conventional multi-filament fibers.

FIG. 20 shows an intersectional point of a suture for sewing a medical device composed of a sheath-core type hybrid filament 44 of FIG. 16, and a conventional multi-filament fiber 49 which is not a hybrid filament. Since this drawing shows the state before heat treatment, the suture for sewing a medical device 44 having the original shape of a core axis and sheath set together, where 45 is a core axis composed of a high-melting point component, and 46 is a sheath composed of a low-melting point component. A conventional multifilament 49 has almost the same temperature as that of the high-melting point component of the core axis part of the suture for sewing a medical device 44 which has a heat fusing feature.

Figure 21:
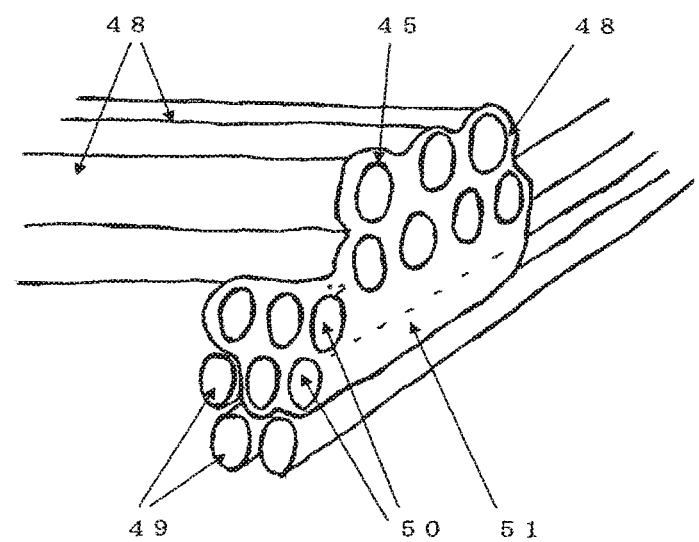
FIG. 21 is a cross-sectional view of the fused state of the intersectional point shown in FIG. 20.

As shown in FIG. 21, at the intersectional point of the suture of this invention and a conventional filament 49 which does not have a low-melting point component, a low-melting point component 46 melts by heat treatment, and part of the melted component covers the filaments 49 which does not have a low-melting point component. Additionally, part of the melted component also invades gaps among the filaments, and solidifies. Even on an intersectional point of the conventional filament which does not have a low-melting point component, the intersectional point becomes glued after heat treatment. In the drawing, 48, which was originally a sheath, is melted and glued to the surroundings by the low-melting point component, and appears as if it is a mono filament. Besides, there is a high-melting point component 45, which was originally contained in a core axis, remaining inside of 48 even after heat treatment, while 48 shows the melted and solidified state of a low-melting point component, which was a sheath, after heat treatment. Along with fusion of hybrid filaments, simultaneously, part of fused low-melting point component invades gaps among filaments of a conventional multifilament 49 and solidifies. Therefore, part of conventional multifilament fibers 50 of 49 can be glued to hybrid filaments 48 by a low-melting point component 51, which has invaded gaps of multi filament 49. By such a phenomenon, heat treatment on an intersectional point of a heat fusible suture and a conventional multi filament can be firmly fused as one body without tying them together. Of cause, by tying a hybrid filament with a conventional filament together, a low-melting point component 51 of a hybrid filament of a knot is melted and invades gaps of multifilament fiber 49 and becomes one body more solidly.

Figure 22:
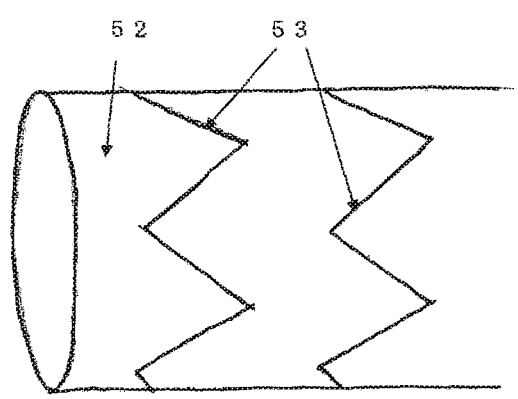
FIG. 22 shows the image of a stent graft illustrating how the wire mesh, which is the expanding part, is sutured onto a tube fabric.
Figure 23:
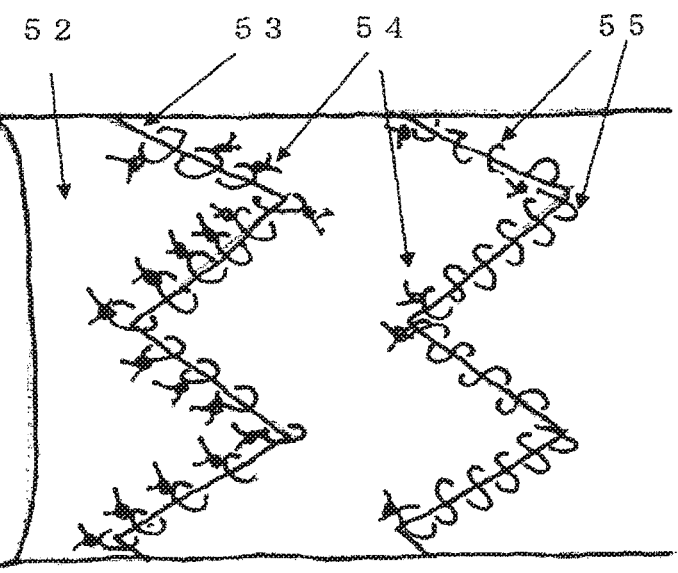
FIG. 23 shows the image of a stent graft illustrating suture parts of FIG. 22 which are sewn according to two different conventional methods.

FIG. 22 shows an image of a stent graft which is sutured a metal stent 53, which is the expanding part, to a tube fabric 52. In general, the fabric is made of polyester fiber, and the stent of the expanding part is made of NiTi-based alloy. Suturing of two materials having different nature by a suture is generally performed. FIG. 23 is an image of the stent graft which sutures the metal stent 53, which is an expanding part, to the tube fabric 52 by a conventional suturing technique. As shown as the image of 54, metal stent 53 is sewn to a fabric 52 by knot suturing method (ligature with each needle stitch to form a knot). This method has an advantage that even if one knot becomes loose, said loose knot does not influence the other parts, but, has a disadvantage that many knots become bulky. Besides, as shown in 55, continuous suturing method is also used conventionally. In the latter case, the thread becomes less bulky because of less numbers of knot, however, there is a fear that partial loosening may cause general loosening. To avoid said problem, generally, knots 54 are formed here and there. Nevertheless, when a stent graft is folded into a small shape, and inserted into a sheath, there is a fear of untying or loosing of these knots.

Figure 24:
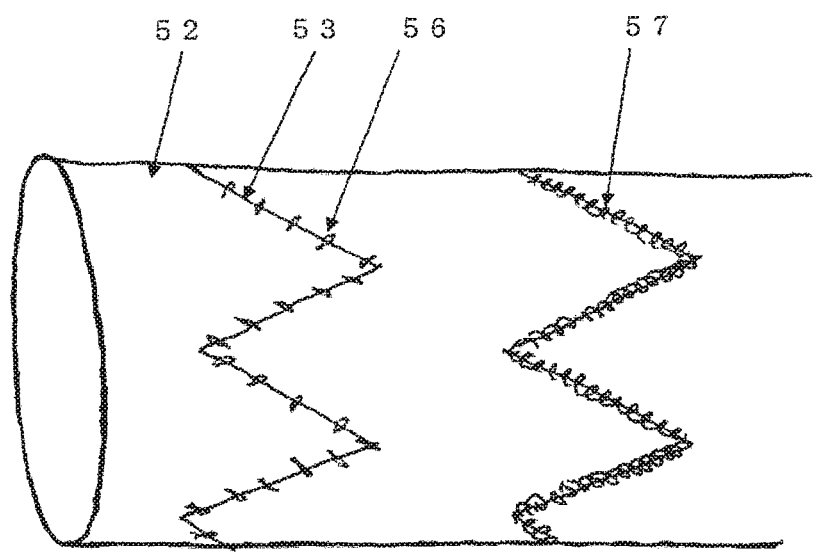
FIG. 24 shows the image of a stent graft illustrating the suture part of FIG. 22 in which the stent wire mesh is sewn according to the method of the present invention.
Figure 25:
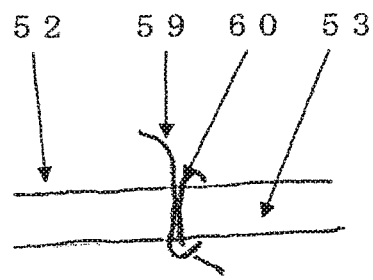
FIG. 25 shows the position where a metal stent wire (53) is fixed to a tube fabric by a suture.
Figure 26:
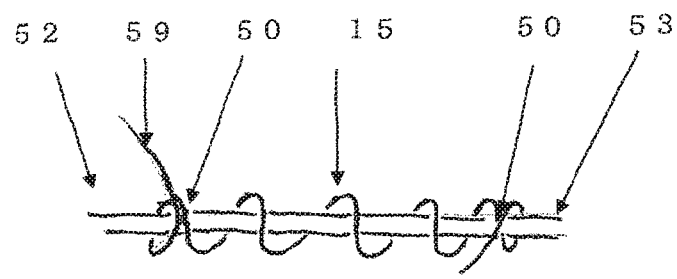
FIG. 26 shows the positions where a metal stent wire (53) is fixed to a tube fabric (52) by a continuous suturing method.

FIG. 24 shows an image of the stent graft prepared by suturing a metal stent 53, which is an expanding part, to a tube fabric 52 according to the method of the present invention. In this case, it is not necessary to form a knot with each needle stitch, as shown in 56, even though the method is similar to the knot suturing method 54 in FIG. 23. The reason can be explained in FIG. 25, which shows a sutured stent graft of a metal stent 53, which is the expanding part, to a tube fabric 52. The method shown in FIG. 25 looks similar to the knot suturing method shown in FIG. 24, but it is not necessary to form a knot with each needle stitch. When the metal stent 53 is sewn to the fabric 52, since a cross-section 60 of the suture 53 is fused by heat, the seam does not become loose with less knots or even without knots, if the heat fusible suture of the present invention is used. As shown in FIG. 26, even by a continuous suturing method, if a suture is crossed at the ends of the suture, cross-sections 50 are fixed by fusion, and can display the anti-loosening effect.

Figure 27:
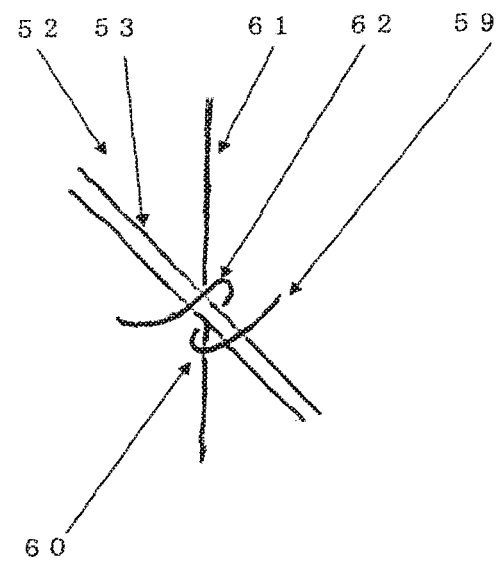
FIG. 27 shows the position where a metal stent wire (53) is fixed to a tube fabric (52) to which a suture (61) of the present invention was previously incorporated by a continuous suturing method.

FIG. 27 is another example showing the suturing method of a metal wire 53, which is an expanding part, to a tube fabric 52. This suturing method does not need to form a knit, although it looks similar to a continuous suturing method. The suture 61 is made according to the present invention, and incorporated in a tube fabric 52. The suture 59 is made according to the present invention, and used for sewing. When the suture 59 of the present invention, which has a heat fusion feature, crosses the suture 61 of the present invention, the crossing part 60 is fused by heat, and fixed. Further, when the suture 59 passes through a fabric made of such an ordinary non heat fusible multifilament fiber as shown in FIG. 21, the suture 59 is heat fused, and fixed. Therefore, also in this case, there is no fear that the suture part will become loose.

Figure 28:
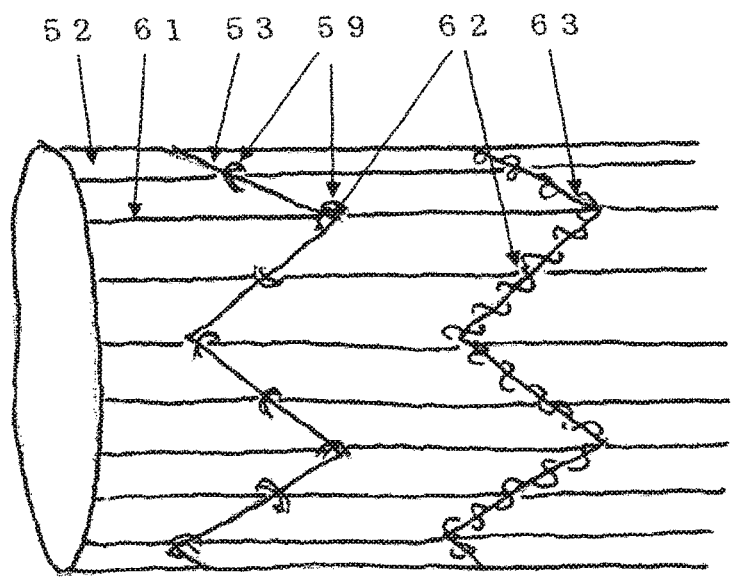
FIG. 28 shows an image of a stent graft consisting of a metal stent (53) which was sewn to a tube fabric (52) to which the suture (61) of the present invention had been previously incorporated by the method of the present invention.

FIG. 28 illustrates a stent wire 53 in its fixed state when using a stent graft fiber 52 in part of which suture 61 was previously incorporated according to the present invention. Suture 61 contacts with sutures 59 and 63 at the cross points 62, and is fused by heat. Thus, quite firm fixation can be obtained using suture 61 of the present invention, even by continuous suturing 63.

The method how to display said effect at the preparation process of the stent graft is practically explained according to FIG. 28. When the heat fusible suture of the present invention is contained as the warp or woof of a fabric, the heat fusible suture and suture used for suturing are fused together by heating after the expanding part is sutured, thus, a strong fixation was obtained without loosening at the expanding part. This less bulky fixation makes it possible to fold a stent graft into a thin shape, and insert it into a narrow sheath.

Figure 29:
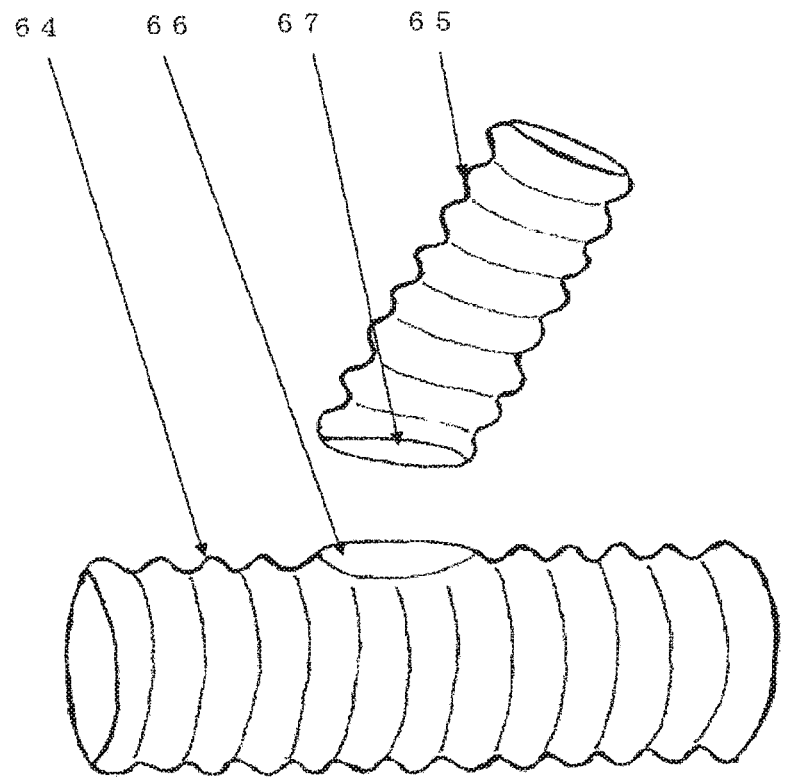
FIG. 29 shows an artificial vascular graft made of polyester fabric and a branch before anastomosis.
Figure 30:
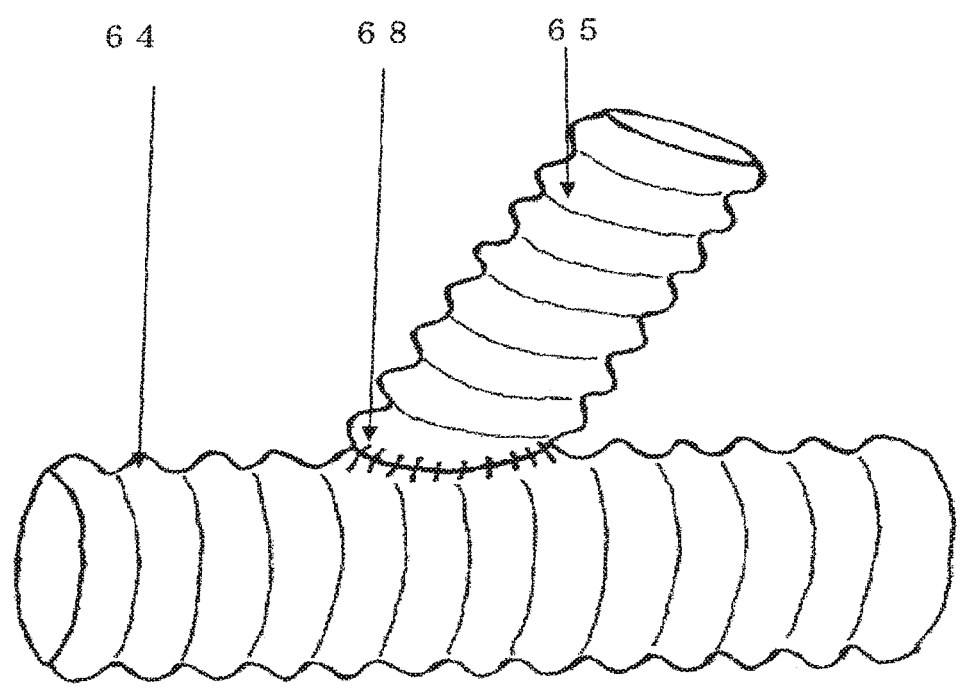
FIG. 30 shows an artificial vascular graft with a branch. The anastomosis was created by a conventional method.

FIG. 29 shows an explanatory view which sews a branch 65 to an artificial vascular graft 64 made of polyester fabric. As shown in the drawing, a bellows structure is provided to the artificial vascular graft and to the branch artificial vascular graft by means of heat set process. At the process to sew the branch artificial vascular graft to the artificial vascular graft, a hole 66 is made on side wall of the artificial vascular graft and these two are sewn 56 by adjusting the cut end of the branch vascular graft to the hole 66 which is made on the side wall of the artificial vascular graft using an ordinary suture. FIG. 30 is an explanatory view showing that the branch 65 is sewn to the artificial vascular graft 64 made of polyester fabric, that is, the cut end of the branch vascular graft is adjusted with the hole 66 made on the side wall of the artificial vascular graft, and sewn using an ordinary suture. This method is used in practice generally, and it is not necessary to suture tightly and reliably to the cut end of the artificial vascular graft to become loose or the seam becomes loose. Accordingly, the seam part becomes thick and hard and the flexibility of the artificial vascular graft is lost. However, if sewn so as to maintain the flexibility of the artificial vascular graft, a fear that the seam will loosen will be caused. In this case, for the sewing of shunt part, a suture which uses ordinary polyester fiber is used, and careful suturing is performed for the suture part not to become loose. Consequently, the seam part becomes hard, and the flexibility of the artificial vascular graft can be easily lost.

Figure 31:
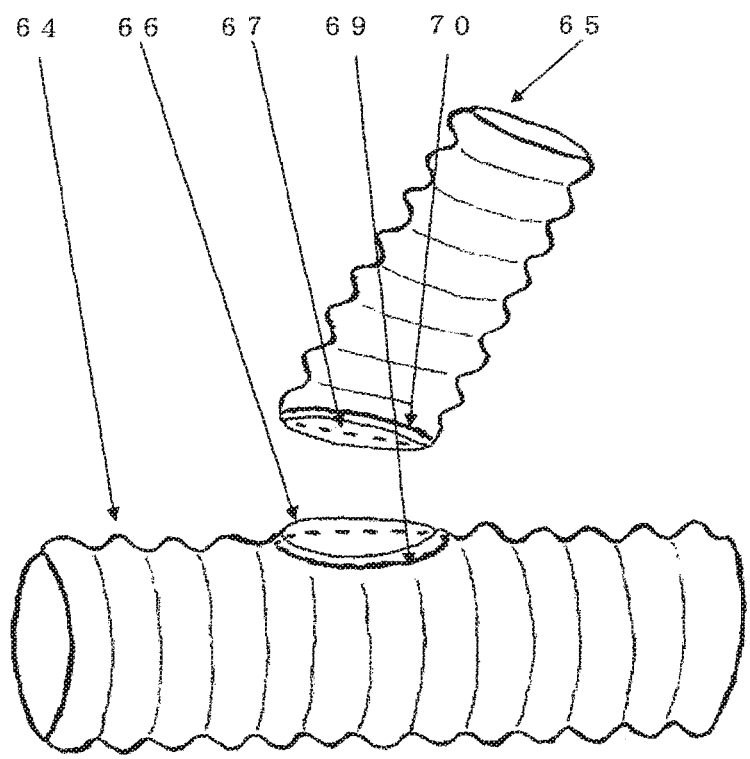
FIG. 31 shows the sewn part of a branch to a trunk artificial vascular graft made of polyester fabric according to the present invention. The sutures of the present invention were incorporated at the site of anastomosis between the cut edge of the branch cut edge and the hole of the trunk.
Figure 32:
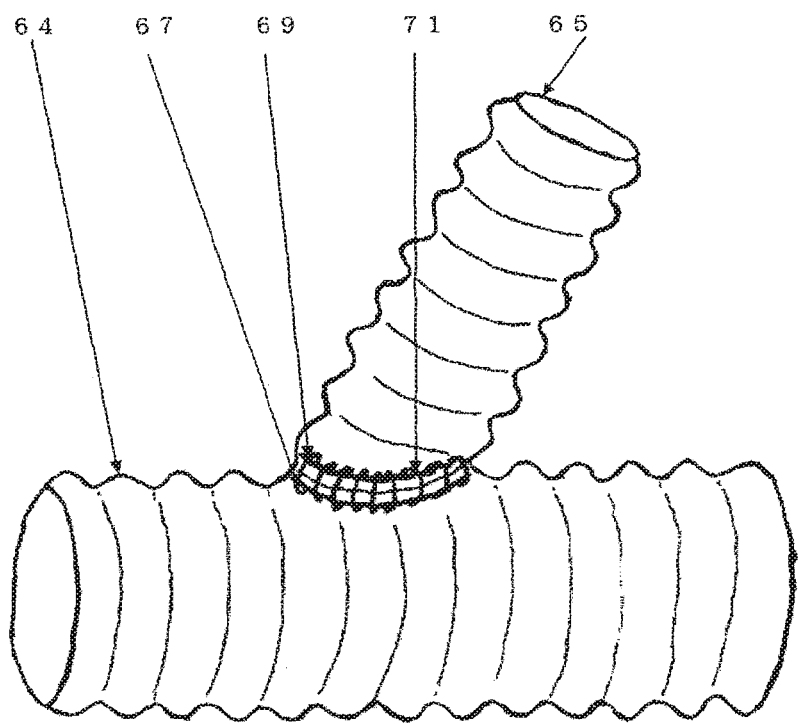
FIG. 32 shows the anastomotic site illustrating the artificial vascular graft of FIG. 31. The stitching was performed using the suture of the present invention. After the stitching and heat treatment, the anastomotic site is firmly fixed by the melted sutures of the present invention.

FIG. 31 shows an explanatory view indicating the sewing process of the branch 65 to the artificial vascular graft 64 made of a polyester fabric according to the method of the present invention. At the sewing of the branch 65, the suture 69 of the present invention is previously tucked in surrounding the hole 66 made on the side wall of the artificial vascular graft. Further, the suture 70 of the present invention is previously tucked in to the cut end of the branch 65 which is the expected position to be sutured. After these previous arrangements, these two artificial vascular grafts are sutured with the suture of the present invention. FIG. 32 is an explanatory view showing that the branch 65 is sutured to the artificial vascular graft 64 made of polyester fabric by the method of the present invention. After the abovementioned arrangement, these two are sutured by using the suture of the present invention. After that the temperature is elevated to the temperature where the low-melting point compound melts. By melting the low-melting point compound, not only the ordinary fiber of the shunt part but also the suture of the present invention are fused and fixed and form one body. Consequently, a problem of loosening at a seam part is solved. Accordingly, a shunt suture having a firm bond used in conventional technique becomes not necessary, and the flexibility of an artificial vascular graft at the shunt part can be maintained.

EXAMPLES

The present invention will be illustrated clearly by the following Examples. The aim of the present invention is to obtain a seam or knot which does not become loose when sewn using the suture of the present invention. These Examples are not intended to restrict the present invention.

Example 1

Kemit resin (registered trademark: polyester copolymer), which has a melting point of 180° C., and is a product of Toray Co. Ltd., was used as a low melting point component. As a high melting point polyester resin, NES-2040 resin (polyethylene terephthalate, a product of Unitika Co. Ltd.) which has a melting point of 260° C., was used.

Kemit resin was spun and drawn by three-fold extension in hot water, and a filament of 30 dtex was obtained. Then NES-2040 resin was spun and drawn by three-fold extension in hot water, and a filament of 10 dtex was obtained. Then, 10 filaments of each were put together to form a bundle. 2 bundles of the former and 8 bundles of the latter, a total of 10 bundles, were braided and a braided suture was prepared as shown in FIG. 2. On the surface of the prepared suture, Kemit fibers, which were the low-melting point component, were exposed along its entire length. The cantilever value of the prepared suture was 5 cm. The tensile strength of the suture was 5.8 Newtons. The thickness corresponded closely to the 4-0 thread of the Japan Pharmaceutical Affairs Law classification. A surgical knot was made in the prepared suture and the tensile strength was measured; the obtained result was 5.8 Newtons. Deterioration of the tensile strength by forming the knot was not observed. The suture in which the knot was made was heated to a temperature of 190° C. The low-melting point component melted and the knot was fixed by heat fusing. Further, all the low-melting point component including the knot also melted, while the high-melting point component did not melt and remained intact. The melted low-melting point component was fixed surrounding the high-melting point component. The tensile strength after heat treatment was measured. The obtained result was 5.6 Newtons. The tensile strength loss was negligible. The melted low-melting point component remained on the suture. The high melting point component fiber did not lose its strength. A 60-time acceleration test was applied to the suture with the fused knot in which pulsatile tensile stress was applied using a Bose vibration load acceleration test machine. The total number of vibrations was set at 32,000,000. This number corresponds to the number of pulsations per year in a living body. The knots of 10 sutures did not loosen, but maintained their original state.

Comparative Example 1

A suture was prepared using a high melting point polyester resin alone. Filaments made from the aforementioned NES-2040 resin, a product of Unitika Co., Ltd., were used. Ten filaments were put together to form a thick bundle. Then 10 thick bundles were twisted to prepare a suture. The cantilever value of the prepared suture was 4 cm. The tensile strength of the suture was 8.0 Newtons. The thickness corresponded closely to the 4-0 thread of the Japan Pharmaceutical Affairs Law classification. A surgical knot was made in the prepared suture and its tensile strength was measured; the obtained result was 7.8 Newtons. Deterioration of the tensile strength in the knot was not observed. Ten sutures in which a knot was tied but not fused were loaded using the Bose vibration load acceleration test machine. The total number of vibrations was set at 32,000,000. This number corresponds to the number of pulsations per year in a living body. In this case, all of the knots of the 10 sutures became loose. From this result, it was concluded that in a case of no-fused sutures, when tensile stress was applied repeatedly, all of the knots became loose.

Comparative Example 2

A suture was prepared by the same method as Example 1, except for using the Kemit resin with a melting point of 235° C. was used instead of the 180° C. melting point Kemit resin. Both are high-melting point resin products of Toray Co., Ltd. The difference between these two high-melting points was 25° C. The tensile strength of the prepared suture was 6.0 Newton. The thickness corresponded closely to the 4-0 thread of the Japan Pharmaceutical Affairs Law classification. A surgical knot was made in the prepared suture, and the tensile strength was measured. The obtained result was 5.9 Newton. Deterioration from tensile stress on the knot was not observed. When the suture in which the knot was formed was heated at a temperature of 235° C., the low-melting point component hardly melted. After that, the suture with its knot was further heated at a temperature of 240° C. In this case, the low-melting point component melted and the knot was fused. Further, all the low-melting point component including the knot melted, while the high-melting point component did not melt and remained unchanged. The melted low-melting point component was firmly fixed to the surrounding high-melting point component. The tensile strength was measured at this stage; the obtained result was 4.6 Newtons. When treated at a temperature higher than 240° C., the filaments of the high-melting point component were damaged and the tensile strength of the suture was lost. Thus, it becomes clear that the melting point of the low-melting point component must differ from that of the high-melting point component by more than 30° C. in order to prevent damage to the strength of the suture.

Comparative Example 3

A suture having low-melting point polyester resin multifilament fibers as its axis was created. The multifilament fibers were made of the 180° C. melting point resin which was used in Example 1. A polyester resin with a melting point of 260° C. was also used. The suture was composed of bundles of both types of fibers. Two bundles of the former filaments and 8 bundles of the latter filaments were braided. In the suture, the 180° C. resin was incorporated into the axis of the suture and was surrounded by the 260° C. resin. Thus, a suture in which the low-melting point component did not appear on the surface of the thread was prepared. The cantilever value of the prepared suture was 5 cm. The whole surface of the suture was occupied by the high-melting point component and the low-melting point component was not seen on the surface. The tensile strength of the prepared suture was 5.8 Newtons. The thickness corresponded closely to the 4-0 thread of the Japan Pharmaceutical Affairs Law classification. A surgical knot was made in the prepared suture, and the tensile strength was measured. The obtained result was 5.8 Newtons. The knot formation did not cause loss of the suture's original strength. The suture on which the knot was formed was heated to a temperature of 200° C. In this treatment, although the fibers became hard, the knot was not fixed by fusion. Fibers of the high-melting point component did not melt, and held the fused low-melting point component inside. The tensile strength of the suture was measured in this state. The obtained result was 5.6 Newtons, and deterioration of the tensile strength was negligible. Ten sutures with knot formation and heat treatment were loaded using the Bose vibration load acceleration test machine. The number of vibrations was set to 32,000,000, which corresponds to the number of pulsations per year in a living body. The results showed that all knots of the 10 sutures had become loose. That is, if at least a part of the low melting point compound was not exposed on the whole length of the surface of the suture, fusion of the suture knots did not work effectively.

Example 2

A method of coating multifilament fibers composed of a high-melting point compound with a low-melting point component resin was tested. First, the multifilament fibers were prepared using a high-melting point polyester resin alone, and a braided multifilament yarn similar to Comparative Example 1 was prepared. To the braided yarn, a melted resin of a low-melting point compound of a polyethylene terephthalate copolymer (melting point is 130° C.) prepared using sebacic acid as a copolymer component was provided by a rotating roller. The melted resin was coated around the braided yarn. In microscopic observation, the surface of the multifilament yarn was completely covered by the low-melting point component, making it appear to be a monofilament suture. A cross-section of the monofilament suture showed that the low-melting point component covered the suture surface and infiltrated the interstices of the braided multifilaments of the high melting point component, so that synthetically it appeared to be a monofilament suture. The cantilever value of the prepared suture was 5 cm. The tensile strength of the suture was 8.1 Newtons. The thickness corresponded closely to the 4-0 thread of the Japan Pharmaceutical Affairs Law classification. A surgical knot was made in the prepared suture and the tensile strength was measured. The obtained result was 8.0 Newtons, and no loss of tensile strength caused by the knot was observed. The suture with its knot was heated to a temperature of 190° C. With this heat treatment, the low-melting point component melted and the knot was fixed by heat fusion. The low-melting point component including the knot melted but the high-melting point component did not melt and remained unchanged. The melted low-melting point component was fused and fixed to the surrounding high-melting point component. The tensile strength after heat treatment was measured. The obtained result was 8.0 Newtons. Loss of tensile strength was not recognized. Since the melted low-melting point component did not drop off the suture but adhered to the high-melting point component by fusion, the suture sustained no strength loss after the heat treatment. Ten sutures with one knot each were loaded using the Bose vibration load acceleration test machine. The number of vibrations was set at 32,000,000. This number corresponds to the number of pulsations per year in a living body. The results showed that all the knots of the 10 sutures had not loosened but maintained their original state.

Example 3

A sheath-core hybrid type filament consisting of a high-melting point resin component, NES-2040, as a core, and a low melting point resin component, Kemit resin, as a sheath, where the core/sheath ratio was 80/20, was spun and drawn with a three-time extension in hot water, and a filament of 30 dtex was obtained. Ten of these filaments were twisted together to form a bundle. Eight of the bundles were braided together to make a braided suture. The cantilever value of the prepared suture was 4.5 cm. The low melting point Kemit resin was exposed along the whole surface of the suture. The tensile strength of the suture was 5.6 Newtons. The thickness corresponded closely to the 4-0 thread of the Japan Pharmaceutical Affairs Law classification. A surgical knot was tied in the prepared suture and the tensile strength was measured. The obtained result was 5.5 Newtons, and deterioration of tensile strength caused by the knot was not observed. The suture with its knot was heated to 180° C. The low melting point component did not melt at the temperature. Then the suture with its knot was then heated to 190° C. At this temperature the low-melting point component melted and the knot was fixed by heat fusion. The high-melting point component did not melt but remained unchanged. The low-melting point component was fused in a position surrounding the high-melting point component. The tensile strength after heat treatment was measured. The obtained result was 5.5 Newtons. Loss of tensile strength was not recognized. The suture with its heat-fused knot was then loaded using the Bose vibration load acceleration test machine. The number of vibrations was set to 32,000,000. This number corresponds to the number of pulsations number per year in a living body. None of the knots in the 10 sutures cases became loose, but maintained their original state.

Example 4

An eyeless needle was with a hollow tail was swaged to the suture prepared in Example 1. The needle as 13 mm and had a curve of 3/8. A fabric vascular graft (LP: Inter Vascular Co. Ltd.) made of polyester fibers was sutured with this needle and suture. Observed under a microscope, the holes made by the needle were filled by the suture, so that there was no danger of blood leakage. Thus, it was clear that suture prepared in Example 1 brought the desirable result of narrowing the needle hole.

Example 5

The same eyeless needle as in Example 4 was swaged to the suture prepared in Examples 2 and 3, and an Inter Vascular LP fabric vascular graft was sutured by the same method. As in Example 4, the needle holes were filled by the suture, and no excessive space was noticed. Therefore, there was no danger of blood leakage from the needle holes.

Comparative Example 5

The suture prepared in Comparative Example 1 was attached to a surgical needle. An Inter Vascular LP fabric vascular graft was sutured with the prepared suture. There was excessive space in the holes where the suture passed through. Therefore, there was danger of blood leakage from the needle holes.

Example 6

This is an example of preparing a medical device by suturing a metal wire mesh to a medical material made of fabric. A fabric tube of 32 mm in inner diameter was prepared by plain weaving using a yarn of 1.2 dtex polyester fiber, which is commercially available, and the tube was used for a stent graft. The water permeability of the fabric was 200 ml. A "z" shaped stent having 6 piles at both ends was prepared using NiTi-based alloy wire mesh of 0.3 mm in diameter. The prepared stent was sutured to the fabric by continuous suturing with the suture and surgical needle prepared in Example 4. The stent was then heated at a temperature of 190° C. The suture was fixed by heat fusion at the seam, so that the seam was completely fixed. Then, mechanical massage was repeated 10 times, but no loosening was observed. The prepared stent graft was inserted in a sheath (15F sheath) of 5 mm diameter and was pushed out from the sheath. This procedure was repeated 10 times. No loosening of the sutured part was observed in any case.

Comparative Example 6

The fabric for a stent graft used in Example 6 and a "z" shape stent were sewn together by continuous stitching using the suture to which a surgical needle was attached as in Comparative Example 5. The knots were tied firmly by surgical methods. The prepared stent graft was mechanically massaged 10 times, and loosening was observed at three ligation points out of 10. After suturing the stent into a sheath (15F sheath) of 5 mm in diameter it was implanted surgically and the stent graft was pushed from the sheath 10 times. Loosening was observed at all of the knots of the suture, and at 4 piles in of the 6 piles in the "z" shaped stent, the stent wire had separated from the fabric. Consequently, it was obvious that when using conventional sutures, there is the danger that the stent will separate from the fabric after loading.

Example 7

A fabric tube of 32 mm in inner diameter was prepared by plain weaving using a yarn of 1.2 dtex polyester fiber. For preparation of the tube, the fibers of 120 dtex prepared in Example 1 having high-melting point fibers and low-melting point fibers at the ratio of 2:1 were mixed together. Then, in the warp, these fibers were braided at the ratio of 1 in 10. Thus, a fabric tube made of fabric containing heat fusible fibers inside was obtained. Then, the stent used in Example 6 was sewn to the fabric tube by continuous suturing with the suture and the swaged needle prepared in Example 4. The suture was subjected to heat treatment at 190° C. All the sutured parts were fixed by the heat fusion. Mechanical massage was repeated 10 times, but no loose points were observed. Further, after suturing the stent graft into a sheath (15F sheath) of 5 mm in diameter, the graft was implanted surgically. It was then pushed out of the sheath 10 times, but no loosening of the sutured part was observed in any case. When observed with a scanning electron microscope, the suture was seen to be partially fused and fixed firmly to the fibers in the fabric. Therefore, it is clear that even after any mechanical massage, there is no danger that the sutured part will become loose or that the stent will separate.

Example 8

A hole was made on the side wall of an Inter Vascular LP made of polyester fiber of 30 mm inner diameter, which was available commercially, and an Inter Vascular LP product of 8 mm inner diameter was sutured to the hole to make a perpendicular anastomosis in the form of the letter T. Continuous suturing with the suture and swaged needle prepared in Example 4 was done, and the anastomosis was heated to a temperature of 190° C. The suture fused at the sutured part became firmly fixed. Mechanical massage was repeated 10 times, but no loosening was observed.

Comparative Example 7

A hole was made on the side wall of an Inter Vascular LP made of polyester fiber of 30 mm inner diameter, which was available commercially, and an Inter Vascular LP product of 8 mm inner diameter was sutured to the hole to make a perpendicular anastomosis in the form of the letter T. Continuous suturing with the suture and needle prepared in Comparative Example 4 was done. A surgical knot was tied firmly as in surgical ligation. Mechanical massage was applied 10 times to the sutured part of the branch, and two of the knots became loose. Consequently, it is seen that there is danger of the knots loosing when mechanical stress is applied to the sutured part if it has been sutured with a conventional suture.

Example 9

As explained in Example 8, a hole was made on the side wall of an artificial vascular graft whose inner diameter was 30 mm, concurrently, the inner periphery of the hole was sewn around the hole with the suture and swaged needle as prepared in Example 4. Then, the cut end of an artificial vascular graft whose inner diameter was 8 mm was sewn around the edge with the suture and swaged needle of the present invention as prepared in Example 4. These two artificial vascular grafts were then sewn together with the same suture swaged needle as prepared in Example 4, and heated at the temperature of 190° C. In consequence, the suture was heat fused and fixed firmly at the anastomosis. Observed with a scanning electron microscope, the suture was fixed to the ordinary fibers without heat fusion features. Heat fusible fibers in the fabric were also fixed firmly inside the fabric, as if they had roots there. Therefore, it is can be seen that even if mechanical massage was applied, there was no fear of loose knots.

Example 10

This Example shows an example of sewing a polyester fiber fabric to the site of a heart valve using heat fusible suture. Polyester mesh of 0.5 mm was sewn to the stent site of a 2-lobe artificial heart valve made of pyrite carbon using the suture and swaged needle prepared in Example 4. Firm surgical knots were made by continuous suturing. At the temperature of 190° C., sutures near the knots were heat fused and fixed. Mechanical massage was applied 10 times to the sutured parts of the prepared stent site of the heart valve, but there was no loosening or fraying of the knots.

Comparative Example 8

Polyester mesh whose mesh size was 0.5 mm was sewn to the stent site of a 2-lobe artificial heart valve made of pyrite carbon using a suture with a surgical needle prepared in Comparative Example 5. Firm knots were made by continuous suturing surgically. Then mechanical massage was applied 10 times to the sutured part of the prepared stent site of the heart valve; two loose knots were observed. Consequently it is clear that when a conventional suturing method or a conventional suture is used, when any mechanical impulse is applied, there is danger of the knot loosening.

Example 11

In a sea-island type hybrid fiber, poly-polyolefin copolymer resin (melting point 145° C.) composed of polyethylene/polypropyrene/polybutene was used as the matrix of the sea-island type, which corresponds to a low-melting point component. As the island part, polyethylene terephthalate (melting point 260° C.), which is a high-melting point component, was used, and a fiber composed of filaments with 16 islands and a sea/island ratio of 25/75 was obtained. This fiber was drawn by a non-contact type heat drawing machine at 80° C., and a fiber of 75 dtex-16 filaments, with a thermal shrinkage ratio of 9%, was obtained. Using this fiber, the same twisted suture as in Example 1 was prepared. The same experiments as in Example 10 were performed using this suture, and the knots were uniformly tightened. No loosening after mechanical massage was observed.

The invention claimed is:

1. A method of making a stent graft, the method comprising:
   providing a fabric made of polyester fiber;
   providing a NiTi-based alloy wire;
   providing a thermally shrinkable suture comprising a
      high-melting point component and a low-melting point component, wherein a difference of melting points between the high-melting point component and the low-melting point component is 30° C. or more and the low-melting point component is exposed on a surface of the suture along a whole length thereof, wherein a thermal shrinkage ratio of the thermally shrinkable suture is 5% or more;

suturing the fabric made of polyester fiber to the NiTi-based alloy wire with the suture at a sutured site;

fusion heating the sutured site at a temperature that melts the low-melting point component but does not melt the high-melting point component; and thermally shrinking the suture.

2. The method of claim 1, wherein the suture is a multifilament fiber wherein the high-melting point component comprises a filament with a high-melting point and the low-melting point component comprises a filament with a low-melting point.

3. The method of claim 1, wherein the suture is a hybrid type filament composed of the high-melting point component and the low-melting point component, further the hybrid type filament is at least one selected from a group consisting of side by side type, sea-island type, dividing type, and sheath-core type filaments.

4. The method of claim 1, wherein the suture is a fiber composed of the high-melting point component which is coated and impregnated with the low-melting point component.

5. A stent graft comprising:
a fabric made of polyester fiber;
a NiTi-based alloy wire; and
a thermally shrinkable suture comprising a high-melting point component and a low-melting point component, wherein a difference of melting points between the high-melting point component and the low-melting point component is 30° C. or more and the low-melting point component is exposed on a surface of the thermally shrinkable suture along a whole length thereof, wherein a thermal shrinkage ratio of the thermally shrinkable suture is 5% or more;

the fabric made of polyester fiber being connected to the NiTi-based alloy wire with the thermally shrinkable suture at a sutured site;

the sutured site having the low-melting point component fused to the low-melting point component.

6. The stent graft of claim 5, wherein the thermally shrinkable suture is a multifilament fiber wherein the high-melting point component comprises a filament with a high-melting point and the low-melting point component comprises a filament with a low-melting point.

7. The stent graft of claim 5, wherein the thermally shrinkable suture is a hybrid type filament composed of the high-melting point component and the low-melting point component, further the hybrid type filament is at least one selected from a group consisting of side by side type, sea-island type, dividing type, and sheath-core type filaments.

8. The stent graft of claim 5, wherein the thermally shrinkable suture is a fiber composed of the high-melting point component which is coated and impregnated with the low-melting point component.

* * * * *